United States Patent
Naito

(10) Patent No.: US 8,512,317 B2
(45) Date of Patent: Aug. 20, 2013

(54) TREATMENT APPARATUS

(75) Inventor: Kimihiko Naito, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 30 days.

(21) Appl. No.: 13/191,183

(22) Filed: Jul. 26, 2011

(65) Prior Publication Data

US 2012/0022509 A1    Jan. 26, 2012

Related U.S. Application Data

(63) Continuation of application No. PCT/JP2010/069143, filed on Oct. 28, 2010.

(30) Foreign Application Priority Data

Mar. 3, 2010  (JP) ................................. 2010-046927

(51) Int. Cl.
*A61B 17/28*  (2006.01)

(52) U.S. Cl.
USPC ............... 606/1; 606/205; 606/206; 606/207; 606/208

(58) Field of Classification Search
USPC ............. 606/1, 139, 144, 167, 170, 174, 180, 606/205–208; 128/749, 751
See application file for complete search history.

(56) References Cited

U.S. PATENT DOCUMENTS

| | | | |
|---|---|---|---|
| 4,708,578 A | 11/1987 | Richter | |
| 5,439,478 A | 8/1995 | Palmer | |
| 6,569,105 B1 * | 5/2003 | Kortenbach et al. | 600/562 |
| 2008/0077159 A1 | 3/2008 | Madhani et al. | |
| 2009/0024141 A1 | 1/2009 | Stahler et al. | |

FOREIGN PATENT DOCUMENTS

| | | |
|---|---|---|
| JP | A-60-76993 | 5/1985 |
| JP | A-2002-543865 | 12/2002 |
| JP | A-2007-215787 | 8/2007 |
| JP | A-2009-142513 | 7/2009 |

OTHER PUBLICATIONS

International Search Report in International Application No. PCT/JP2010/069143; dated Nov. 30, 2010 (with English-language translation).

European Search Report from the European Patent Office for corresponding European Patent Application No. 10847039.4 dated Feb. 13, 2012.

* cited by examiner

*Primary Examiner* — Aaron Roane
(74) *Attorney, Agent, or Firm* — Oliff & Berridge, PLC

(57) ABSTRACT

A treatment apparatus includes a rotor which is provided between a distal-end treatment section and a flexible tube section and which is rotatable together with the distal-end treatment section in the periaxial directions with respect to the flexible tube section, a rotational operation wire which is configured to be pulled or loosened by a rotational operation section to rotate the distal-end treatment section, and a wire fixing portion which is provided to the rotor or to a part to the distal-end direction side of the rotor and to which a distal end of the rotational operation wire is fixed. The treatment apparatus includes a direction change portion which is configured to change an extending direction of the rotational operation wire extended on an outer peripheral surface of the rotor from the wire fixing portion, and configured to lead out the rotational operation wire to the rotational operation section.

9 Claims, 11 Drawing Sheets

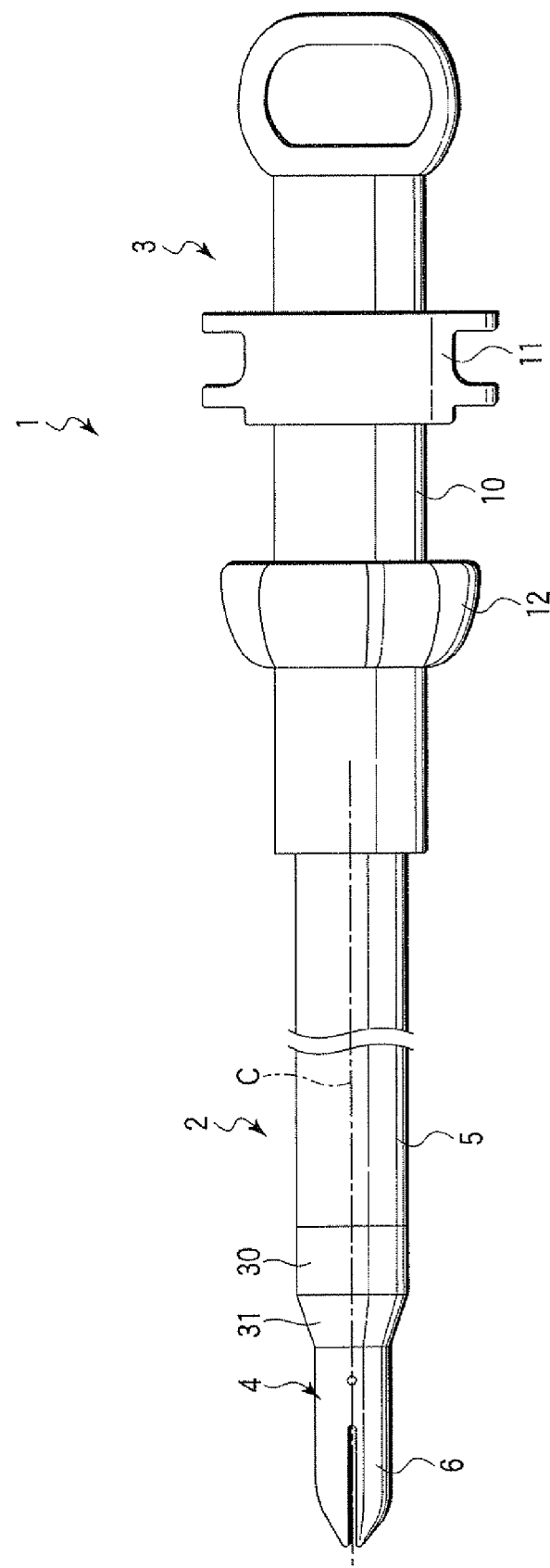
F I G. 1

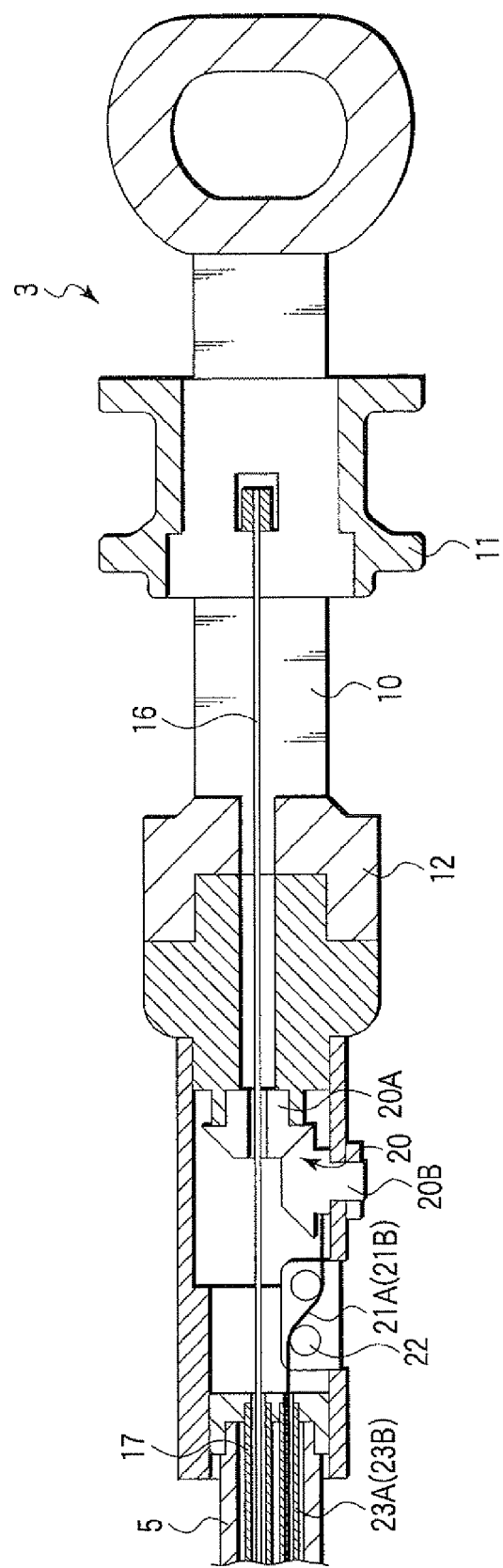
F I G. 2

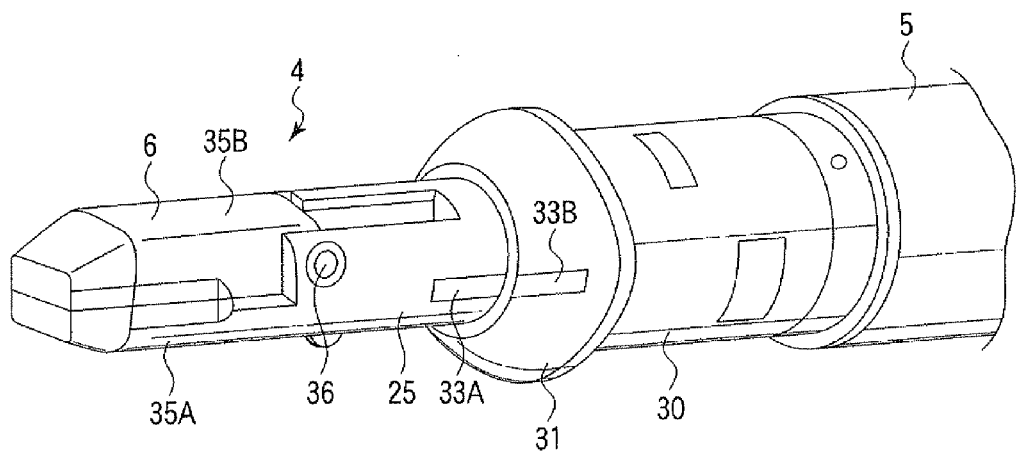
F I G. 3
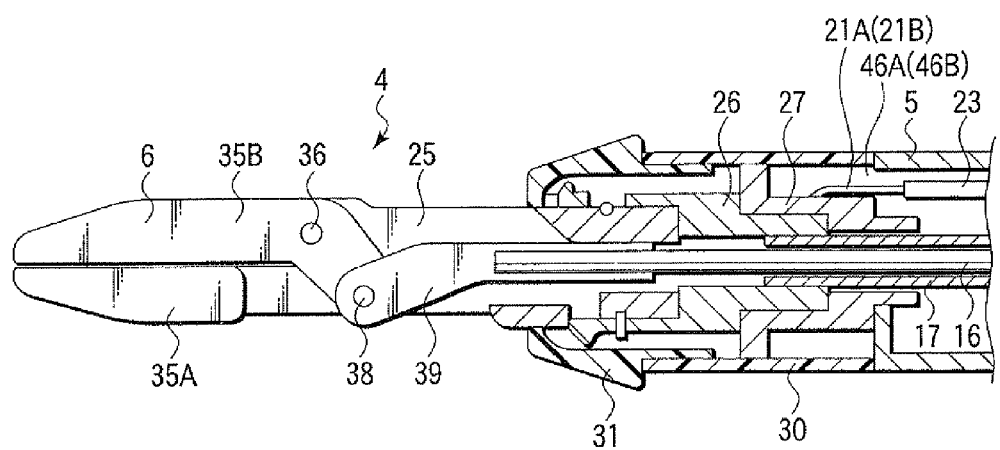
F I G. 4

TREATMENT APPARATUS

CROSS-REFERENCE TO RELATED APPLICATIONS

This is a Continuation Application of PCT Application No. PCT/JP2010/069143, filed Oct. 28, 2010, which was published under PCT Article 21(2) in Japanese.

This application is based upon and claims the benefit of priority from prior Japanese Patent Application No. 2010-046927, filed Mar. 3, 2010, the entire contents of which are incorporated herein by reference.

BACKGROUND OF THE INVENTION

1. Field of the Invention

The present invention relates to a treatment apparatus such as a forceps or a manipulator which is configured to be inserted into a body cavity of a patient and to treat a diseased part.

2. Description of the Related Art

JP-A 2009-142513 (KOKAI) discloses a high-frequency treatment apparatus configured to grip a diseased part with high-frequency electrodes to give a treatment. This high-frequency treatment apparatus includes an insertion section configured to be inserted into a body cavity and an operation section provided to a proximal-end direction side of the insertion section. The insertion section includes a distal-end treatment section to which the high-frequency electrodes are provided, and a flexible tube section which is provided to the proximal-end direction side of the distal-end treatment section and which is extended in longitudinal directions. When performing a rotational action of the distal-end treatment section, rotating torque is transmitted to the distal-end treatment section through a conductive wire, which is a rotational operation transmitting member inserted into the flexible tube section, by rotating the operation section. As a result, the distal-end treatment section rotates in periaxial directions with respect to the flexible tube section.

Further, a treatment apparatus including a motor provided at a distal-end treatment section is also used. In this treatment apparatus, the distal-end treatment section performs a rotational action by driving the motor.

Furthermore, there is also used a treatment apparatus in which a bevel gear is provided to a distal-end treatment section and the distal-end treatment section performs a rotational action by rotating the bevel gear. In this treatment apparatus, a rotational operation transmitting member such as a wire, which is inserted into a flexible tube section, is connected to the bevel gear. The bevel gear rotates by pulling or loosening the wire, and the distal-end treatment section rotates in periaxial directions with respect to the flexible tube section.

BRIEF SUMMARY OF THE INVENTION

According to one aspect of the invention, a treatment apparatus includes a flexible tube section which has a longitudinal axis and is extended in longitudinal directions, a distal-end treatment section which is provided to a distal-end direction side of the flexible tube section and which is rotatable in periaxial directions with respect to the flexible tube section, a rotor which is provided between the distal-end treatment section and the flexible tube section and which is rotatable together with the distal-end treatment section in the periaxial directions with respect to the flexible tube section, a rotational operation section which is provided to a proximal-end direction side of the flexible tube section and which is configured to perform a rotational operation of the distal-end treatment section, a rotational operation wire which is configured to be pulled or loosened by the rotational operation section to rotate the distal-end treatment section, a wire fixing portion which is provided to the rotor or to a part to the distal-end direction side of the rotor and to which a distal end of the rotational operation wire is fixed, and a direction change portion which is configured to change an extending direction of the rotational operation wire extended on an outer peripheral surface of the rotor from the wire fixing portion, and configured to lead out the rotational operation wire to the rotational operation section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a treatment apparatus according to a first embodiment of the present invention;

FIG. 2 is a cross-sectional view showing a configuration of an operation section of the treatment apparatus according to the first embodiment;

FIG. 3 is a perspective view showing a configuration of a distal-end direction side part of the treatment apparatus according to the first embodiment;

FIG. 4 is a cross-sectional view showing the configuration of the distal-end direction side part of the treatment apparatus according to the first embodiment;

DETAILED DESCRIPTION OF THE INVENTION

First Embodiment

Figure 5:
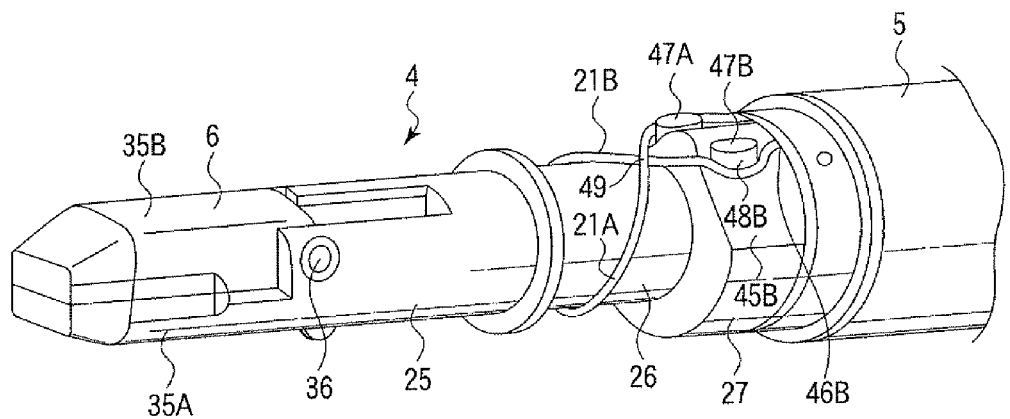
FIG. 5 is a perspective view showing the distal-end direction side part of the treatment apparatus according to the first embodiment in a state that a first cover and a second cover are removed.

A first embodiment according to the present invention will now be described with reference to FIG. 1 to FIG. 11.

FIG. 1 is a view showing a configuration of a treatment apparatus 1 according to this embodiment. As shown in FIG. 1, the treatment apparatus 1 includes an insertion section 2 configured to be inserted into a body cavity and an operation section 3 provided to a proximal-end direction side of the insertion section 2. The insertion section 2 includes a distal-end treatment section 4 configured to give a treatment, and a flexible tube section 5 provided to the proximal-end direction side of the distal-end treatment section 4 and extended in longitudinal directions. A grip section 6 configured to grip a tissue and the like is provided in the distal-end treatment section 4. Moreover, the flexible tube section 5 has a longitudinal axis C.

FIG. 2 is a view showing a configuration of the operation section 3. As shown in FIG. 2, the operation section 3 includes an operation section main body 10, a grip operation handle 11 as a grip operation section configured to perform a grip operation of gripping, e.g., a tissue by the grip section 6, and a rotational operation handle 12 as a rotational operation section configured to perform a rotational operation of rotating the distal-end treatment section 4 in periaxial directions of the flexible tube section 5.

The grip operation handle 11 is attached to the operation section main body 10 in a state that the grip operation handle 11 is movable in the longitudinal directions with respect to the operation section main body 10. A proximal end of a grip operation wire 16 as a grip operation transmitting member configured to transmit a grip operation to the grip section 6 is fixed to the grip operation handle 11. A distal end of the grip operation wire 16 is connected to the grip section 6 of the distal-end treatment section 4 through the inside of the flexible tube section 5. In the flexible tube section 5, the grip operation wire 16 is inserted in a coil pipe 17 used in the grip operation. When the grip operation handle 11 is moved in the longitudinal directions with respect to the operation section main body 10, the grip operation wire 16 is pulled or loosened.

The rotational operation handle 12 is attached to the operation section main body 10 in a state that the rotational operation handle 12 can rotate in the periaxial directions of the operation section main body 10. A bevel gear 20 is coupled with the rotational operation handle 12. The bevel gear 20 includes a first gear 20A coupled with the rotational operation handle 12, and a second gear 20B that meshes with the first gear 20A. Proximal ends of a first rotational operation wire 21A and a second rotational operation wire 21B as rotational operation transmitting members configured to transmit the rotational operation to the distal-end treatment section 4 are connected to the second gear 20B. The first rotational operation wire 21A and the second rotational operation wire 21B are guided to the inside of the flexible tube section 5 by a guide pulley 22 and extended in the flexible tube section 5 along substantially the longitudinal directions. In the flexible tube section 5, each of the first rotational operation wire 21A and the second rotational operation wire 21B is inserted into associated rotational operation coil pipe 23A or 23B. For example, the first rotational operation wire 21A is inserted into the coil pipe 23A. When the rotational operation handle 12 is rotated in the periaxial directions, the first gear 20A of the bevel gear 20 rotates together with the rotational operation handle 12 in the periaxial directions. With the rotation of the first gear 20A, the second gear 20B rotates about an axis orthogonal to the longitudinal directions. When the second gear 20B rotates in one of rotational directions, the first rotational operation wire 21A is pulled, and the second rotational operation wire 21B is loosened. When the second gear 20B rotates in the other of the rotational directions, the first rotational operation wire 21A is loosened, and the second rotational operation wire 21B is pulled.

FIG. 3 and FIG. 4 are views each showing a distal-end direction side part of the treatment apparatus 1. As shown in FIG. 3 and FIG. 4, a rotor 26 is provided between the distal-end treatment section 4 and the flexible tube section 5 in a state that the rotor 26 is fixed in the distal-end treatment section 4. A rotor support member 27 is provided between the rotor 26 and the flexible tube section 5. The rotor support member 27 is coupled with and fixed to the flexible tube section 5. The rotor 26 is coupled with the rotor support member 27 to be rotatable in the periaxial directions thereof. A cylindrical first cover 30 is provided to an outer peripheral direction side of the rotor support member 27. The first cover 30 is fixed to and coupled with the flexible tube section 5. A truncated conical second cover 31 is provided to the distal-end direction side of the first cover 30 to be fixed to the first cover 30. Adopting such a configuration enables the distal-end treatment section 4 and the rotor 26 to integrally rotate in the periaxial directions with respect to the flexible tube section 5, the rotor support member 27, the first cover 30, and the second cover 31.

It is to be noted that, as shown in FIG. 3, a first mark 33A may be provided on an outer peripheral surface of the distal-end treatment section 4, and a second mark 33B may be provided on an outer peripheral surface of the second cover 31. As a result, an operator confirms a positional relationship between the first mark 33A and the second mark 33B from an image of, e.g., an endoscope used together with the treatment apparatus 1. Further, a neutral position (an initial position) of the distal-end treatment section 4 and amounts of the rotation of the distal-end treatment section 4 from the neutral position in the periaxial directions with respect to the flexible tube section 5 can be recognized from the positional relationship between the first index 33A and the second index 33B.

As shown in FIG. 3 and FIG. 4, the distal-end treatment section 4 includes a treatment section main body 25. A first pinch portion 35A constituting the grip section 6 is provided at a distal-end direction side part of the treatment section main body 25. Additionally, a second pinch portion 35B constituting the grip section 6 is supported to swing by the treatment section main body 25 through a coupling pin 36. The second pinch portion 35B can rotate together with the treatment section main body 25 in the periaxial directions with respect to the flexible tube section 5. Further, the second pinch portion 35B can rotate about the coupling pin 36 with respect to the treatment section main body 25. When the second pinch portion 35B rotates with respect to the treatment section main body 25, the second pinch portion 35B performs opening or closing action with respect to the first pinch portion 35A of the treatment section main body 25.

As shown in FIG. 4, the grip operation coil pipe 17 into which the grip operation wire 16 is inserted is coupled with the rotor 26 through the flexible tube section 5 and the rotor support member 27 in a state that a distal end of the grip operation wire 16 is fixed to the rotor 26. The grip operation wire 16 is further extended to the distal-end direction side of the distal end of the coil pipe 17. A coupling member 39 coupled with the second pinch portion 35B through the coupling pin 38 is provided in the treatment section main body 25. A distal end of the grip operation wire 16 is fixed to the coupling member 39 through the rotor 26. Adopting such a configuration enables the coupling member 39 to move in the longitudinal directions in response to a pulling or loosening action of the grip operation wire 16 when the grip operation wire 16 is pulled or loosened by an operation of the grip operation handle 11. Based on the movement of the coupling member 39, the second pinch portion 35B performs a rotating action about the coupling pin 36 with respect to the treatment section main body 25. When the coupling member 39 moves in the distal-end direction, the second pinch portion 35B rotates in a direction where the second pinch portion 35B opens with respect to the first pinch portion 35A. On the other hand, when the coupling member 39 moves in the proximal-end direction, the second pinch portion 35B rotates in a direction where the second pinch portion 35B closes with respect to the first pinch portion 35A.

Figure 6:
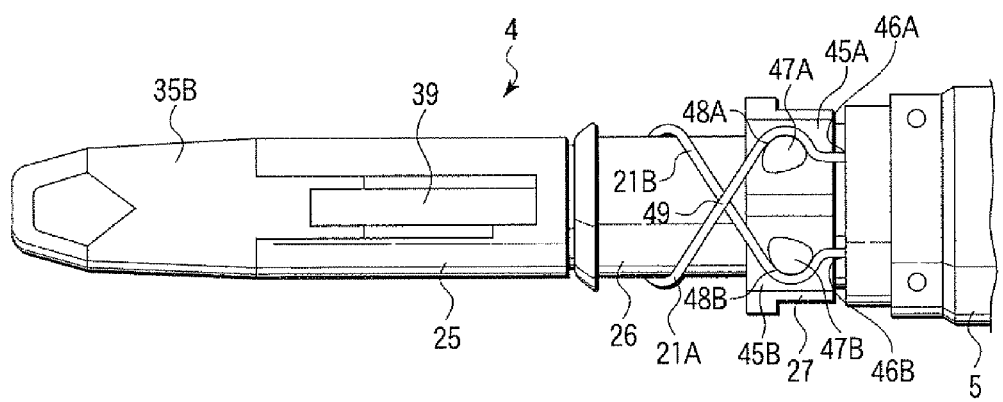
FIG. 6 is a plan view showing the distal-end direction side part of the treatment apparatus according to the first embodiment in the state that the first cover and the second cover are removed.
Figure 7:
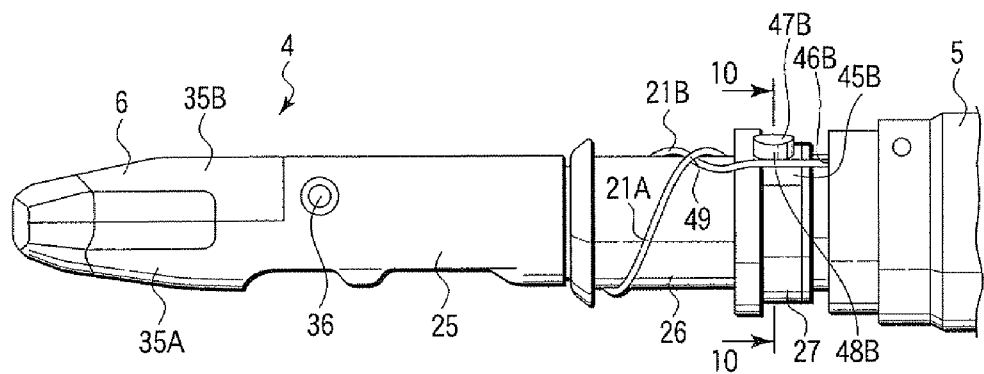
FIG. 7 is a side view showing the distal-end direction side part of the treatment apparatus according to the first embodiment in the state that the first cover and the second cover are removed.
Figure 8:
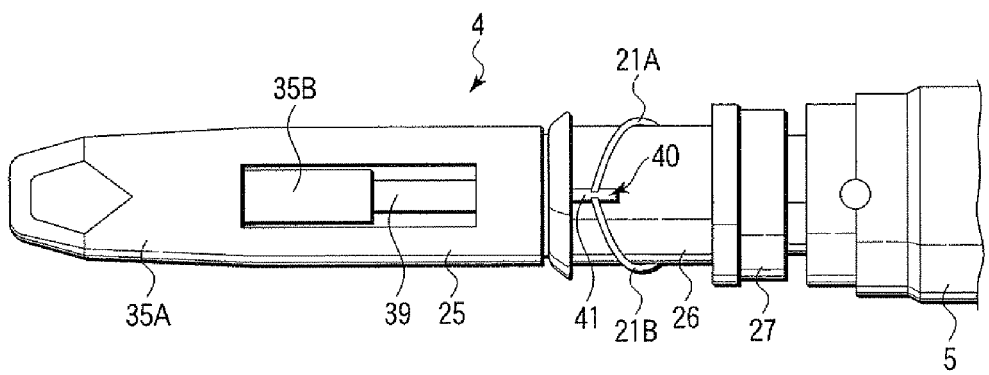
FIG. 8 is a bottom view showing the distal-end direction side part of the treatment apparatus according to the first embodiment in the state that the first cover and the second cover are removed.

FIG. 5 to FIG. 8 are views each showing a configuration of the distal-end direction side part of the treatment apparatus 1 in a state that the first cover 30 and the second cover 31 are removed. As shown in FIG. 8, a through hole 41 pierced in the rotor 26 in a radial direction is provided in a distal-end direction side part of the rotor 26.

Figure 9:
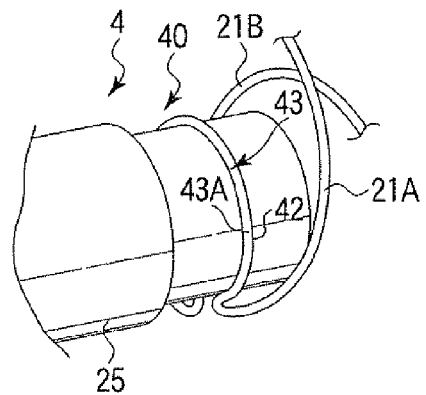
FIG. 9 is a perspective view showing a configuration of a wire fixing portion to which ends of a first rotational operation wire and a second rotational operation wire are fixed in the treatment apparatus according to the first embodiment.

FIG. 9 is a view showing a configuration of a wire fixing portion 40 configured to fix distal ends of the first rotational operation wire 21A and the second rotational operation wire 21B. As shown in FIG. 9, a groove portion 42 is provided along circumferential directions on a part of the treatment section main body 25 (the distal-end treatment section 4) placed to an inner peripheral direction side of the rotor 26. One linear member 43 is wound and fixed on the groove portion 42 by, e.g., brazing, thereby forming a wound portion 43A. The linear member 43 is extended from both ends of the wound portion 43A to the outer peripheral direction side of the rotor 26 via the through hole 41. A portion extended to the outer peripheral direction side of the rotor 26 from one end of the wound portion 43A of the linear member 43 forms the first rotational operation wire 21A, and a portion extended to the outer peripheral direction side of the rotor 26 from the other end of the wound portion 43A forms the second rotational operation wire 21B.

It is to be noted that the first rotational operation wire 21A and the second rotational operation wire 21B are formed of the one linear member 43 in this embodiment in consideration of efficiency of an assembling operation of the treatment apparatus and others, but the present invention is not restricted thereto. For example, the first rotational operation wire 21A and the second rotational operation wire 21B may be formed of two different linear members, and each of the linear members may be fixed in the groove portion 42 of the distal-end treatment section 4.

Figure 10:
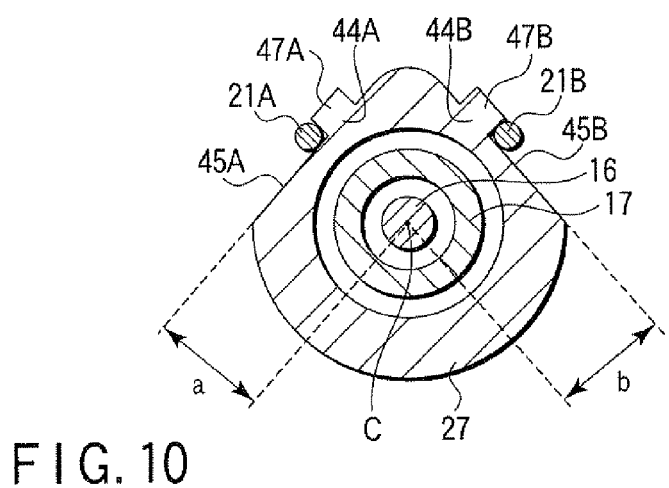
FIG. 10 is a cross-sectional view taken along a line 10-10 in FIG. 7.

FIG. 10 is a cross-sectional view taken along a line 10-10 in FIG. 7. As shown in FIG. 5 and FIG. 10, an outer peripheral surface of the rotor support member 27 includes a first surface 45A and a second surface 45B each of which has a radial distance from the longitudinal axis C of the flexible tube section 5 smaller than those of any other portions of the outer peripheral surface. Each of the first surface 45A and the second surface 45B is formed by flatly cutting the rotor support member 27 in the radial direction, for example. The first surface 45A is arranged at a position apart from the through hole 41 of the rotor 26 in the circumferential directions. The second surface 45B is arranged at a position apart from the through hole 41 of the rotor 26, toward a direction opposite to a direction where the first surface 45A is disposed, in the circumferential directions. A protruding convex portion 47A protruding in the outer peripheral direction is provided on the first surface 45A. Likewise, a second protruding portion 47B protruding in the outer peripheral direction from the outer peripheral surface is provided on the second surface 45B. That is, the first surface 45A is a protruding portion arrangement surface where the first protruding portion 47A is placed, and the second surface 45B is a protruding portion arrangement surface where the second protruding portion 47B is placed. As shown in FIG. 5 and FIG. 6, a first circular surface 48A is provided to the first protruding portion 47A, and a second circular surface 48B is provided to the second protruding portion 47B.

It is to be noted that each of the first surface 45A and the second surface 45B is formed in a planar shape in this embodiment, but the present invention is not restricted thereto. For example, each of the first surface 45A and the second surface 45B may be formed in a curved surface. That is, in each of the first surface 45A and the second surface 45B, a satisfactory configuration is one in which the radial distance from the longitudinal axis C of the flexible tube section 5 is smaller than those of any other portions of the outer peripheral surface of the rotor support member 27. Further, it is preferable that a radius of each of the first circular surface 48A and the second circular surface 48B is not smaller than a minimum bending R of each of the first rotational operation wire 21A and the second rotational operation wire 21B.

As shown in FIG. 5 to FIG. 8, the first rotational operation wire 21A extended from the wire fixing portion 40 toward the outer peripheral direction is extended on an outer peripheral surface of the rotor 26 along a first oblique direction inclined from the longitudinal directions toward the circumferential directions. Furthermore, the first rotational operation wire 21A abuts on the first convex portion 47A along the first circular surface 48A. That is, the first rotational operation wire 21A abuts on the first circular surface 48A of the first convex portion 47A. Since the first rotational operation wire 21A abuts on the first convex portion 47A, the extending direction of the first rotational operation wire 21A is changed from the first oblique direction. A first hole portion 46A is provided at a position to the proximal-end direction side of the first convex portion 47A. The first rotational operation wire 21A whose extending direction has been changed from the first oblique direction by the first convex portion 47A is inserted into the flexible tube section 5 from the first hole portion 46A. That is, the first hole portion 46A is a wire inserting portion through which the first rotational operation wire 21A is inserted into the flexible tube section 5. The first rotational operation wire 21A inserted in the flexible tube section 5 is extended to a rotational operation section (the rotational operation handle 12).

On the other hand, the second rotational operation wire 21B extended from the wire fixing portion 40 toward the outer peripheral direction is extended on the outer peripheral surface of the rotor 26 along a second oblique direction inclined from the longitudinal directions toward the circumferential directions to a direction opposite to the first oblique direction. Moreover, the second rotational operation wire 21B abuts on the second convex portion 47B along the second circular surface 48B. That is, the second rotational operation wire 21B abuts on the second circular surface 48B of the second convex portion 47B. Since the second rotational operation wire 21B abuts on the second convex portion 47B, the extending direction of the second rotational operation wire 21B is changed from the second oblique direction. A second hole portion 46B is provided at a position to the proximal-end direction side of the second convex portion 47B. The second rotational operation wire 21B whose extending direction has been changed from the second oblique direction by the second convex portion 47B is inserted into the flexible tube section 5 from the second hole portion 46B. That is, the second hole portion 46B is a wire inserting portion through which the second rotational operation wire 21B is inserted into the flexible tube section 5. The second rotational operation wire 21B inserted in the flexible tube section 5 is extended to the rotational operation section (the rotational operation handle 12).

As shown in FIG. 5 and FIG. 6, a wire crossing portion 49 at which the first rotational operation wire 21A crosses the second rotational operation wire 21B is provided on the outer peripheral surface of the rotor 26. That is, the wire crossing portion 49 is provided between the wire fixing portion 40 and the first convex portion 47A (the second convex portion 47B). As shown in FIG. 10, a first distance a from an axis center of the rotor support member 27 (the longitudinal axis C of the flexible tube section 5) to the first surface 45A is larger than a second distance b from the axis center of the rotor support member 27 (the longitudinal axis C of the flexible tube section 5) to the second surface 45B. That is, in the first convex portion 47A, a first root 44A is provided to be apart in the radial direction from the longitudinal axis C of the flexible tube section 5 by the first distance a. Further, in the second convex portion 47B, a second root 44B is provided to be apart in the radial direction from the longitudinal axis C of the flexible tube section 5 by the second distance b smaller than the first distance a. Therefore, in the wire crossing portion 49, the first rotational operation wire 21A crosses the second rotational operation wire 21B in a state that the first rotational operation wire 21A is arranged on the outer peripheral direction side and the second rotational operation wire 21B is arranged on the inner peripheral direction side. Here, it is preferable that a difference (a-b) between the first distance a and the second distance b is equal to or above a diameter of each of the first rotational operation wire 21A and the second rotational operation wire 21B. As a result, at the wire crossing portion 49, the first rotational operation wire 21A and the second rotational operation wire 21B cross without coming into contact with each other.

It is to be noted that the first distance a from the axis center of the rotor support member 27 to the first surface 45A may be smaller than the second distance b from the axis center of the rotor support member 27 to the second surface 45B. In this case, at the wire crossing portion 49, the first rotational operation wire 21A and the second rotational operation wire 21B cross each other in a state that the first rotational operation wire 21A is arranged on the inner peripheral direction side and the second rotational operation wire 21B is arranged on the outer peripheral direction side.

A function of the treatment apparatus 1 according to this embodiment will now be described. In the treatment apparatus 1, when rotating the distal-end treatment section 4 in the periaxial directions with respect to the flexible tube section 5, the rotational operation handle 12 is rotated in one of rotating directions. As a result, the first rotational operation wire 21A is pulled and the second rotational operation wire 21B is loosened through the bevel gear 20.

Figure 11:
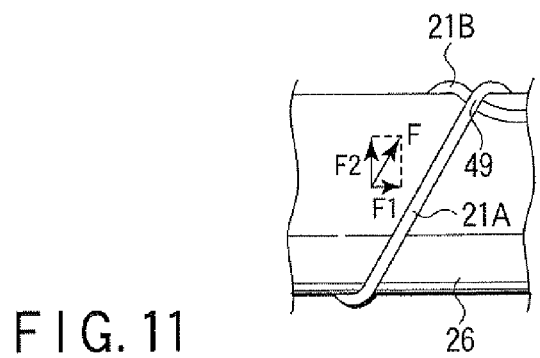
FIG. 11 is a schematic diagram explaining a rotational action of a distal-end treatment section of the treatment apparatus in periaxial directions according to the first embodiment.

FIG. 11 is a view explaining a rotational action of the distal-end treatment section 4 in the periaxial directions. The first rotational operation wire 21A is extended on the outer peripheral surface of the rotor 26 along the first oblique direction inclined from the longitudinal directions toward the circumferential directions between the wire fixing portion 40 and the first convex portion 47A. Therefore, as shown in FIG. 11, when the first rotational operation wire 21A is pulled, force F is applied to the rotor 26 in the first oblique direction. The force F can be divided into force F1 in the longitudinal directions and force F2 in the circumferential directions. The rotor 26 is rotated in one of the rotating directions by the force F2 in the circumferential directions. At this time, the treatment section main body 25 and the second pinch portion 35B (the distal-end treatment section 4) rotate in the periaxial directions together with the rotor 26. As described above, the distal-end treatment section 4 and the rotor 26 rotate in one of the rotating directions with respect to the flexible tube section 5 and the rotor support member 27.

On the other hand, when the rotational operation handle 12 is rotated in the other of the rotating directions, the first rotational operation wire 21A is loosened and the second rotational operation wire 21B is pulled through the bevel gear 20. The second rotational operation wire 21B is extended on the outer peripheral surface of the rotor 26 along the second oblique direction inclined from the longitudinal directions toward the circumferential directions to the direction opposite to the first oblique direction between the wire fixing portion 40 and the second convex portion 47B. Therefore, when the second rotational operation wire 21B is pulled, force is applied to the rotor 26 in the second oblique direction. This force can be divided into force in the longitudinal directions and force in the circumferential directions which acts in a direction opposite to the force F2. The rotor 26 is rotated in the other of the rotating directions by the force that acts in the direction opposite to the force F2. At this time, the treatment section main body 25 and the second pinch portion 35B (the distal-end treatment section 4) rotate in the periaxial directions together with the rotor 26. As described above, the distal-end treatment section 4 and the rotor 26 rotate in the other of the rotating directions with respect to the flexible tube section 5 and the rotor support member 27.

In the treatment apparatus 1, the first rotational operation wire 21A abuts on the first convex portion 47A along the first circular surface 48A, and the second rotational operation wire 21B abuts on the second convex portion 47B along the second circular surface 48B. Therefore, when the first rotational operation wire 21A is pulled, stress applied to the first rotational operation wire 21A from the first convex portion 47A is reduced. Likewise, when the second rotational operation wire 21B is pulled, stress applied to the second rotational operation wire 21B from the second convex portion 47B is reduced. Further, when the radius of the first circular surface 48A of the first convex portion 47A is set to be not smaller than the minimum bending R of the first rotational operation wire 21A, the stress applied to the first rotational operation wire 21A from the first convex portion 47A can be further reduced. This is also true for the second rotational operation wire 21B and the second convex portion 47B.

Furthermore, in the treatment apparatus 1, the wire crossing portion 49 at which the first rotational operation wire 21A crosses the second rotational operation wire 21B is provided at the portion between the wire fixing portion 40 and the first convex portion 47A (the second convex portion 47B) on the outer peripheral surface of the rotor 26. Providing the wire crossing portion 49 causes the distal-end treatment section 4 to be rotatable in the range of at least ±180 degrees from the neutral position (the initial position) when the distal-end treatment section 4 rotates in the periaxial directions of the flexible tube section 5.

Furthermore, the first distance a from the axis center of the rotor support member 27 (the longitudinal axis C of the flexible tube section 5) to the first surface 45A (the first root 44A of the first convex portion 47A) is larger than the second distance b from the axis center of the rotor support member 27 (the longitudinal axis C of the flexible tube section 5) to the second surface 45B (the second root 44B of the second convex portion 47B). Here, when the difference (a-b) between the first distance a and the second distance b is set to be not smaller than the diameter of each of the first rotational operation wire 21A and the second rotational operation wire 21B, the first rotational operation wire 21A and the second rotational operation wire 21B cross without coming into contact with each other at the wire crossing portion 49. As a result, an effect of friction between the first rotational operation wire 21A and the second rotational operation wire 21B at the wire crossing portion 49 is reduced.

Moreover, in the treatment apparatus 1, the first surface 45A and the second surface 45B, each of which has the radial distance from the longitudinal axis C of the flexible tube section 5 being smaller than that of any other portions of the outer peripheral surface, are provided on the outer peripheral surface of the rotor support member 27. Additionally, the first convex portion 47A is provided on the first surface 45A, and the second convex portion 47A is provided on the second surface 45B. Therefore, as compared with a configuration where the first convex portion 47A or/and the second convex portion 47B is/are provided at positions excluding the first surface 45A and the second surface 45B on the outer peripheral surface of the rotor support member 27, a diameter of the distal-end direction side part of the treatment apparatus 1 is reduced.

Therefore, the thus configured treatment apparatus 1 exhibits the following effect. That is, in the treatment apparatus 1 according to this embodiment, when the first rotational operation wire 21A is pulled by an operation using the rotational operation handle 12, the force F is applied to the rotor 26 in the first oblique direction. This force F is divided into the force F1 in the longitudinal directions and the force F2 in the circumferential directions. The rotor 26, the treatment section main body 25, and the second pinch portion 35B (the distal-end treatment section 4) are rotated in one of the rotating directions by the force F2. Likewise, when the second rotational operation wire 21B is pulled by an operation using the rotational operation handle 12, the force is applied to the rotor 26 in the second oblique direction. The force in the second oblique direction is divided into the force in the longitudinal directions and the force in the circumferential directions that acts in the direction opposite to the force F2. The rotor 26, the treatment section main body 25, and the second pinch unit 35B (the distal-end treatment section 4) are rotated in the other of the rotating directions by the force in the direction opposite to the force F2. As described above, since the distal-end treatment section 4 and the rotor 26 rotate in the periaxial directions with respect to the flexible tube section 5 and the rotor support member 27, the rotational operation is appropriately transmitted to the distal-end treatment section 4. Moreover, since a motor, a bevel gear, and others are not provided in the distal-end treatment section 4, the diameter of the distal-end treatment section 4 can be reduced. Therefore, it is possible to provide the treatment apparatus 1 that can realize appropriate transmission of the rotational operation to the distal-end treatment section 4 and reduce the diameter of the distal-end treatment section 4.

Additionally, in the treatment apparatus 1, the first rotational operation wire 21A abuts on the first convex portion 47A along the first circular surface 48A, and the second rotational operation wire 21B abuts on the second convex portion 47B along the second circular surface 48B. Therefore, when the first rotational operation wire 21A is pulled, the stress applied to the first rotational operation wire 21A from the first convex portion 47A can be reduced. Likewise, when the second rotational operation wire 21B is pulled, the stress applied to the second rotational operation wire 21B from the second convex portion 47B can be reduced. Further, when the radius of the first circular surface 48A of the first convex portion 47A is set to be not smaller than the minimum bending R of the first rotational operation wire 21A, the stress applied to the first rotational operation wire 21A from the first convex portion 47A can be further reduced. This is also true for the second rotational operation wire 21B and the second convex portion 47B.

Furthermore, in the treatment apparatus 1, the wire crossing portion 49 at which the first rotational operation wire 21A crosses the second rotational operation wire 21B is provided at the position between the wire fixing portion 40 and the first convex portion 47A (the second convex portion 47B) on the outer peripheral surface of the rotor 26. Providing the wire crossing portion 49 enables the distal-end treatment section 4 to be rotatable in the range of at least ±180 degrees from the neutral position (the initial position) when the distal-end treatment section 4 rotates in the periaxial directions with respect to the flexible tube section 5.

Moreover, in the treatment apparatus 1, the first distance a from the axis center of the rotor support member 27 (the longitudinal axis C of the flexible tube section 5) to the first surface 45A (the first root 44A of the first convex portion 47A) is larger than the second distance b from the axis center of the rotor support member 27 (the longitudinal axis C of the flexible tube section 5) to the second surface 45B (the second root 44B of the second convex portion 47B). Here, when the difference (a-b) between the first distance a and the second distance b is set to be not smaller than the diameter of each of the first rotational operation wire 21A and the second rotational operation wire 21B, the first rotational operation wire 21A crosses the second rotation operation wire 21B without coming into contact with each other at the wire crossing portion 49. As a result, it is possible to reduce the effect of friction between the first rotational operation wire 21A and the second rotational operation wire 21B at the wire crossing portion 49.

Additionally, in the treatment apparatus 1, the first surface 45A and the second surface 45B, each of which has the radial distance from the longitudinal axis C of the flexible tube section 5 being smaller than that of any other portions of the outer peripheral surface of the rotor support member 27, are provided on the outer peripheral surface. Furthermore, the first convex portion 47A is provided on the first surface 45A, and the second convex portion 47A is provided on the second surface 45B. Therefore, as compared with the configuration where the first convex portion 47A or/and the second convex portion 47B is/are provided at positions excluding the first surface 45A and the second surface 45B on the outer peripheral surface of the rotor support member 27, the diameter of the distal-end direction side part of the treatment apparatus 1 is reduced.

Modifications of First Embodiment

A modification of the first embodiment will now be described with reference to FIG. 12 to FIG. 15. It is to be noted that like reference numerals denote the same parts and parts having the same functions as those in the first embodiment, thereby omitting a description thereof.

Figure 12:
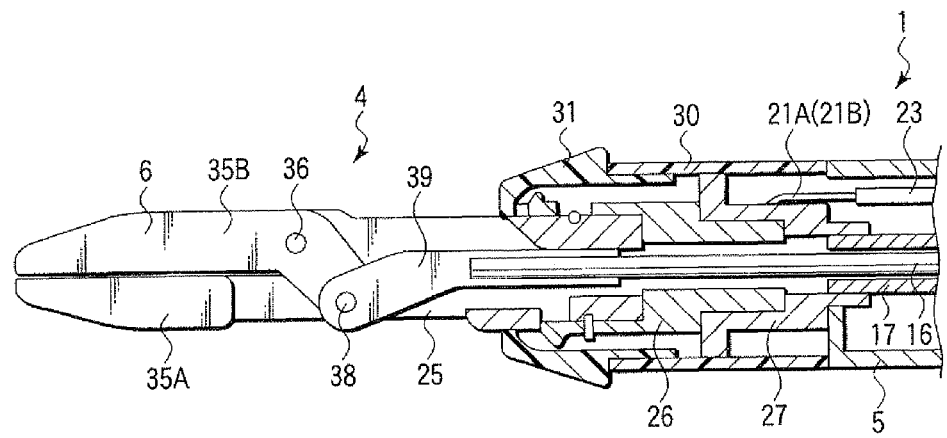
FIG. 12 is a cross-sectional view showing a distal-end direction side part of a treatment apparatus according to a first modification of the first embodiment.

FIG. 12 is a view showing a configuration of a distal-end direction side part of a treatment apparatus 1 according to a first modification of the first embodiment. As shown in FIG. 12, in the treatment apparatus 1 according to this modification, a distal end of a grip operation wire coil pipe 17 into which a grip operation wire 16 is inserted is fixed to and coupled with a rotor support member 27 rather than a rotor 26. When the coil pipe 17 is coupled with the rotor 26, the coil pipe 17 and the grip operation wire 16 integrally rotate with rotor 26 in the periaxial directions at the time of a rotational action of a rotor 26. Therefore, the rotational torque of rotating the rotor 26 is increased. Further, when the grip operation wire coil pipe 17 and the grip operation wire 16 rotate, the grip operation wire 16 is apt to be affected by the friction from other internal members in the flexible tube section 5. Therefore, a diameter of the grip operation wire 16 must be increased to avoid cutting of the grip operation wire 16.

On the other hand, in the treatment apparatus 1 according to this modification, since the grip operation wire coil pipe 17 is coupled with the rotor support member 27, the grip operation wire 16 alone rotates and the coil pipe 17 does not rotate when the rotor 26 performs the rotational action. Therefore, the rotational torque of rotating the rotor 26 can be reduced. Furthermore, when the rotor 26 carries out the rotational action, friction occurs between the grip operation wire 16 and the coil pipe 17. Therefore, as compared with a configuration in which the grip operation wire 16 is affected by the friction from other internal members in the flexible tube section 5, the diameter of the grip operation wire 16 can be reduced.

Figure 13:
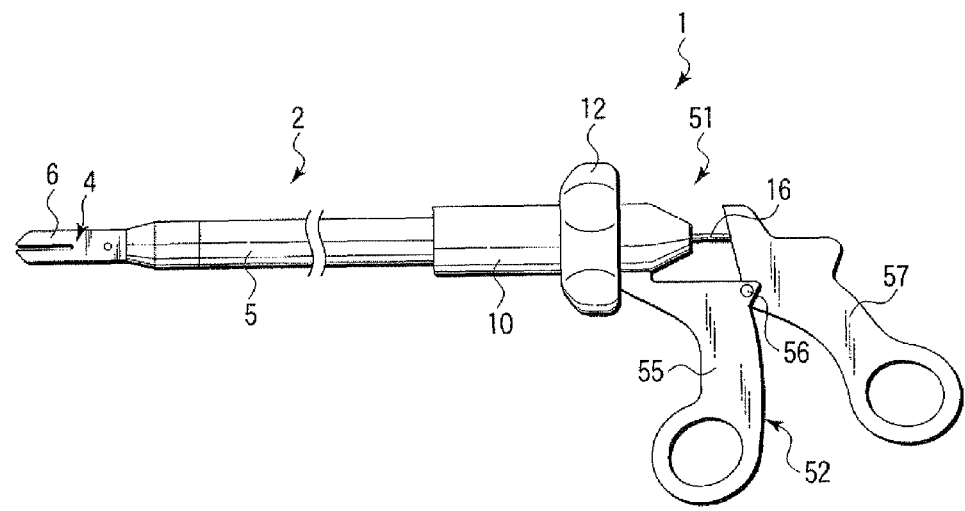
FIG. 13 is a schematic view showing a treatment apparatus according to a second modification of the first embodiment.

FIG. 13 is a view showing a configuration of a treatment apparatus 1 according to a second modification of the first embodiment. As shown in FIG. 13, a grip operation section 52 configured to effect a grip operation of gripping, e.g., a tissue by the grip section 6 is provided in an operation section 51 of the treatment apparatus 1. The grip operation section 52 includes a fixed handle 55 fixed to an operation section main body 10, and a movable handle 57 supported on the fixed handle 55 to swing through a coupling pin 56. The movable handle 57 can rotate about the coupling pin 56 with respect to the fixed handle 55. A proximal end of a grip operation wire 16 is connected to the movable handle 57. When the movable handle 57 is rotated in a closing direction with respect to the fixed handle 55, the grip operation wire 16 is pulled. Furthermore, when the movable handle 57 is rotated in an opening direction with respect to the fixed handle 55, the grip operation wire 16 is loosened.

As described above in conjunction with the second modification, the configuration of pulling or loosening the grip operation wire 16 is not restricted to the configuration of the foregoing embodiment. Likewise, the configuration of pulling or loosening the first rotational operation wire 21A and the second rotational operation wire 21B is not restricted to the configuration of the foregoing embodiment either.

Figure 14:
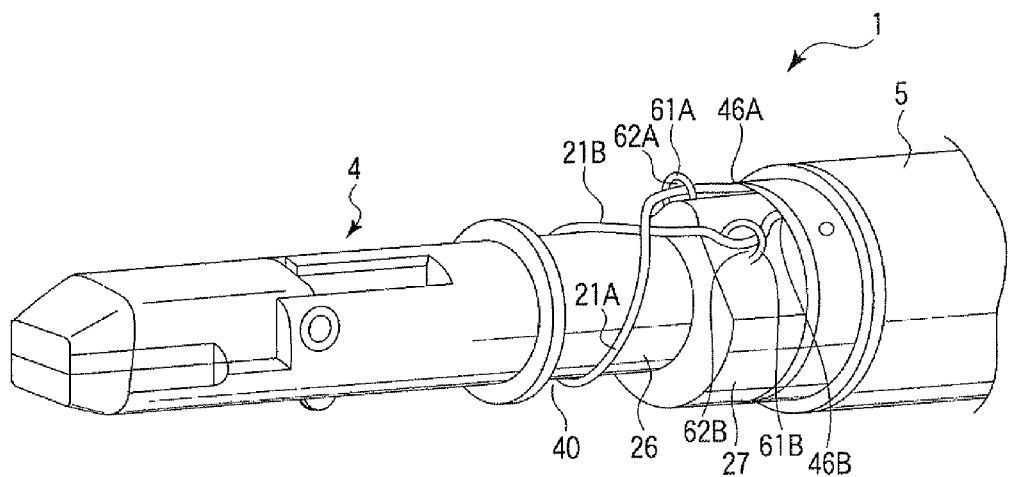
FIG. 14 is a perspective view showing a distal-end direction side part of a treatment apparatus according to a third modification of the first embodiment.

FIG. 14 is a view showing a distal-end direction side part of a treatment apparatus 1 according to a third modification of the first embodiment. As shown in FIG. 14, the first convex portion 47A and the second convex portion 47B are not provided on a rotor support member 27 according to this modification. Instead, a first guide portion 61A and a second guide portion 61B are provided to the rotor support member 27. The first guide portion 61A includes a first insertion hole 62A, and the second guide portion 61B includes a second insertion hole 62B.

As shown in FIG. 14, a first rotational operation wire 21A extended from a wire fixing portion 40 is extended on the outer peripheral surface of a rotor 26 along a first oblique direction inclined from the longitudinal directions toward the circumferential directions. Moreover, the first rotational operation wire 21A is inserted into the first insertion hole 62A of the first guide portion 61A. When the first rotational operation wire 21A is inserted into the first insertion hole 62A of the first guide portion 61A, the extending direction of the first rotational operation wire 21A is changed from the first oblique direction. The first rotational operation wire, the extending direction of which has been changed from the first oblique direction by the first guide portion 61A, is inserted into a flexible tube section 5 from the first hole portion 46A. That is, the first hole portion 46A is a wire inserting portion through which the first rotational operation wire 21A is inserted into the flexible tube section 5. The first rotational operation wire 21A inserted in the flexible tube section 5 is extended to a rotational operation section (a rotational operation handle 12).

On the other hand, a second rotational operation wire 21B extended from the wire fixing portion 40 is extended on the outer peripheral surface of the rotor 26 along a second oblique direction inclined from the longitudinal directions toward the circumferential directions to the direction opposite to the first oblique direction. Further, the second rotational operation wire 21B is inserted into the second insertion hole 62B of the second guide portion 61B. When the second rotational operation wire 21B is inserted into the second insertion hole 62B of the second guide portion 61B, the extending direction of the second rotational operation wire 21B is changed from the second oblique direction. The second rotational operation wire 21B, the extending direction of which has been changed from the second oblique direction by the second guide portion 61B, is inserted into the flexible tube section 5 from the second hole portion 46B. That is, the second hole portion 46B is a wire inserting portion through which the second rotational operation wire 21B is inserted into the flexible tube section 5. The second rotational operation wire 21B inserted in the flexible tube section 5 is extended to the rotational operation section (the rotational operation handle 12).

Figure 15:
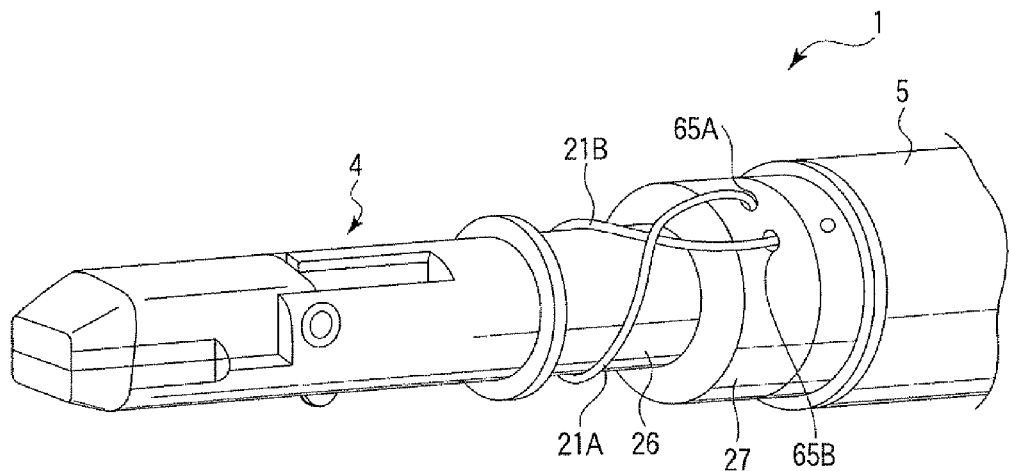
FIG. 15 is a perspective view showing a distal-end direction side part of a treatment apparatus according to a fourth modification of the first embodiment.

FIG. 15 is a view showing a distal-end direction side part of a treatment apparatus 1 according to a fourth modification of the first embodiment. As shown in FIG. 15, the first convex portion 47A and the second convex portion 47B are not provided on a rotor support member 27 according to this modification. Instead, a first hole portion 65A and a second hole portion 65B are provided to the rotor support member 27.

As shown in FIG. 15, a first rotational operation wire 21A extended from a wire fixing portion 40 is extended on the outer peripheral surface of a rotor 26 along a first oblique direction inclined from the longitudinal directions toward the circumferential directions. Further, the first rotational operation wire 21A is inserted into the first hole portion 65A of the rotor support member 27. When the first rotational operation wire 21A is inserted into the first hole portion 65A, the extending direction of the first rotational operation wire 21A is changed from the first oblique direction. Furthermore, the first rotational operation wire 21A is inserted into a flexible tube section 5 from the first hole portion 65A. That is, the first hole portion 65A is a wire inserting portion through which the first rotational operation wire 21A is inserted into the flexible tube section 5. The first rotational operation wire 21A inserted into the flexible tube section 5 is extended to a rotational operation section (a rotational operation handle 12).

On the other hand, a second rotational operation wire 21B extended from the wire fixing portion 40 is extended on the outer peripheral surface of the rotor 26 along a second oblique direction inclined from the longitudinal directions toward the circumferential directions to the direction opposite to the first oblique direction. Furthermore, the second rotational operation wire 21B is inserted into a second hole portion 65B of the rotor support member 27. When the second rotational operation wire 21B is inserted into the second hole portion 65B, the extending direction of the second rotational operation wire 21B is changed from the second oblique direction. Moreover, the second rotational operation wire 21B is inserted into the flexible tube section 5 from the second hole portion 65B. That is, the second hole portion 65B is a wire inserting portion through which the second rotational operation wire 21B is inserted into the flexible tube section 5. The second rotational operation wire 21B inserted into the flexible tube section 5 is extended to the rotational operation section (the rotational operation handle 12).

As described above in conjunction with the third modification and the fourth modification, the configuration in which the extending direction of the first rotational operation wire 21A is changed from the first oblique direction and the configuration in which the extending direction of the second rotational operation wire 21B is changed from the second oblique direction are not restricted to those in the foregoing embodiment. That is, it is satisfactory to provide a direction change portion configured to change the extending direction of the first rotational operation wire 21A, extended from the wire fixing portion 40 on the outer peripheral surface of the rotor 26 along the first oblique direction, from the first oblique direction and to cause the first rotational operation wire 21A to be extended to the rotational operation section. Likewise, it is satisfactory to provide a direction change portion configured to change the extending direction of the second rotational operation wire 21B, extended from the wire fixing portion 40 on the outer peripheral surface of the rotor 26 along the second oblique direction, from the second oblique direction and to cause the second rotational operation wire 21B to be extended to the rotational operation unit.

Further, when the first convex portion 47A is provided as the direction change portion of the first rotational operation wire 21A, the first convex portion 47A includes the first circular surface 48A in the foregoing embodiment, but the first circular surface 48A does not have to be necessarily provided. That is, a satisfactory configuration is one in which the extending direction of the first rotational operation wire 21A is changed from the first oblique direction when the first rotational operation wire 21A abuts on the first convex portion 47A. This is also true for the configuration where the second convex portion 47B is provided as the direction change portion of the second rotational operation wire 21B.

Furthermore, although the first surface 45A and the second surface 45B each of which has the smaller radial distance from the longitudinal axis C of the flexible tube section 5 than those of any other portions of the outer peripheral surface of the rotor support member 27 are provided on the outer peripheral surface in the foregoing embodiment, these surfaces do not have to be necessarily provided. For example, in a state that the radial distances from the longitudinal axis C of the flexible tube section 5 are equal in any portions, the outer peripheral surface of the rotor support member 27 may be formed.

Moreover, the first convex portion 47A and the second convex portion 47B may be provided on the distal-end direction side part of the flexible tube section 5. That is, the first convex portion 47A and the second convex portion 47B may be provided on the distal-end direction side part of the flexible tube section 5 or a different member, e.g., the rotor support member 27 which is provided between the flexible tube section 5 and the distal-end treatment section 4 is fixed to the flexible tube section 5. Additionally, the first surface and the second surface each of which has a smaller radial distance from the longitudinal axis C of the flexible tube section 5 than those of any other parts of the outer peripheral surface may be provided on the distal-end direction side part of the flexible tube section 5. In this case, the first convex portion 47A is provided on the first surface, and the second convex portion 47B is provided on the second surface.

Further, although the distal-end treatment section 4 and the rotor 26 are different members in the foregoing embodiment, they may be integrally formed. That is, the distal-end treatment section 4 and the rotor 26 can be configured to rotate in the periaxial directions with respect to the flexible tube section 5. Furthermore, it is satisfactory to provide the wire fixing portion 40, to which the distal ends of the first rotational operation wire 21A and the second rotational operation wire 21B are fixed, to the rotor 26 or parts to a distal-end direction side of the rotor 26. Moreover, although the distal-end treatment section 4 includes the grip section 6 in the foregoing embodiment, the present invention is not restricted thereto. For example, the distal-end treatment section 4 may be an electric scalpel.

Additionally, although the wire crossing portion 49 is provided on the outer peripheral surface of the rotor 26 between the wire fixing portion 40 and the first convex portion 47A (the second convex portion 47B) in the foregoing embodiment, the wire crossing portion 49 does not have to be necessarily provided. That is, it is satisfactory to cause the first rotational operation wire 21A to be extended on the outer peripheral surface of the rotor 26 along the first oblique direction inclined from the longitudinal directions toward the circumferential directions between the wire fixing portion 40 and the first convex portion 47A. Likewise, it is satisfactory to cause the second rotational operation wire 21B to be extended on the outer peripheral surface of the rotor 26 along the second oblique direction inclined from the longitudinal directions toward the circumferential directions to the direction opposite to the first oblique direction between the wire fixing portion 40 and the second convex portion 47B.

Second Embodiment

A second embodiment according to the present invention will now be described with reference to FIG. 16. It is to be noted that like reference numerals denote the same parts or parts having the same functions as those in the first embodiment, thereby omitting a detailed description thereof.

Figure 16:
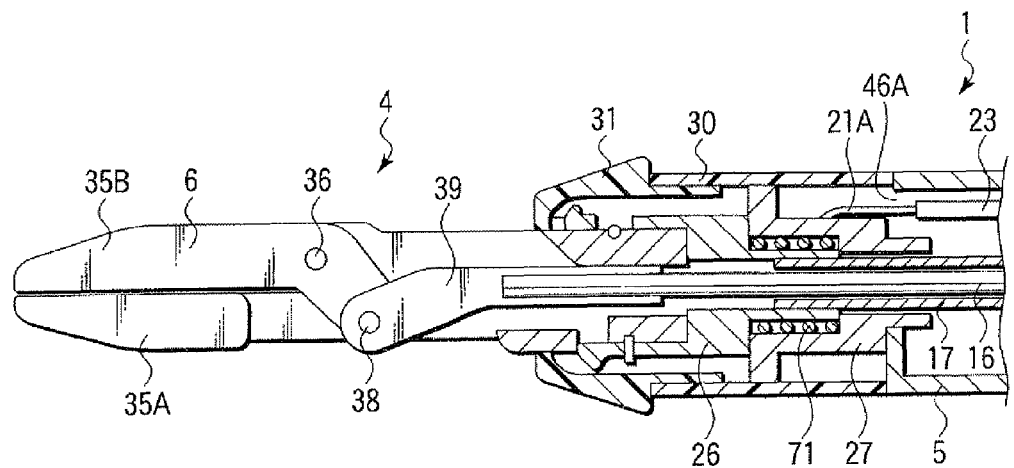
FIG. 16 is a cross-sectional view showing a configuration of a distal-end direction side part of a treatment apparatus according to a second embodiment of the present invention.

FIG. 16 is a view showing a configuration of a distal-end direction side part of a treatment apparatus 1 according to this embodiment. As shown in FIG. 16, a torsion spring 71 is provided on an outer peripheral surface of a rotor 26 according to this embodiment. The torsion spring 71 is arranged to the outer peripheral side of the rotor 26 and to the inner peripheral side of a rotor support member 27. When the torsion spring 71 performs an action, the rotor 26 receives an urging force in one of rotating directions. That is, the torsion spring 71 is an urging member configured to give the urging force in one of the rotating directions of the rotor 26.

Moreover, in the treatment apparatus 1, one rotational operation wire 21A alone is provided in comparison to the first embodiment in which the two rotational operation wires 21A and 21B are provided. Likewise, one convex portion 47A alone is provided on the rotor support member 27.

A distal end of the rotational operation wire 21A is fixed to a wire fixing portion 40 like the first embodiment. The rotational operation wire 21A, the distal end of which is fixed to the wire fixing portion 40, is extended on the outer peripheral surface of the rotor 26 along an oblique direction inclined from the longitudinal directions toward the circumferential directions to a direction opposite to a direction where the torsion spring 71 gives the urging force. Additionally, the rotational operation wire 21A abuts on the convex portion 47A. When the rotational operation wire 21A abuts on the convex portion 47A, the extending direction of the rotational operation wire 21A changes from the oblique direction. The rotational operation wire 21A whose extending direction has been changed from the oblique direction by the convex portion 47 is inserted into a flexible tube section 5 from a hole portion 46A. The rotational operation wire 21A inserted in the flexible tube section 5 is extended to a rotational operation section (a rotational operation handle 12).

A function of the treatment apparatus 1 according to this embodiment will now be described. When effecting a rotational action of a distal-end treatment section 4 in the periaxial directions with respect to the flexible tube section 5, the torsion spring 71 is actuated. The rotor 26 receives the urging force in one of the rotating directions by the action of the torsion spring 71. The rotor 26 rotates in one of the rotating directions by the urging force from the torsion spring 71. At this time, a treatment section main body 25 and a second pinch portion 35B (the distal-end treatment section 4) rotate in the periaxial directions integrally with the rotor 26. As described above, the distal-end treatment section 4 and the rotor 26 rotate in one of the rotating directions with respect to the flexible tube section 5 and the rotor support member 27.

Additionally, the rotational operation wire 21A is pulled by an operation using the rotational operation handle 12. The rotational operation wire 21A is extended on the outer peripheral surface of the rotor 26 between the wire fixing portion 40 and the convex portion 47A along the oblique direction inclined from the longitudinal directions to the circumferential directions to the direction opposite to the direction where the torsion spring 71 gives the urging force. Therefore, when the rotational operation wire 21A is pulled, a force is applied to the rotor 26 in the oblique direction. This force is divided into a longitudinal force and a circumferential force acted to the direction opposite to the urging force from the torsion spring 71. The rotor 26 is rotated in the other of the rotating directions by the force acted to the direction opposite to the urging force from the torsion spring 71. At this time, the treatment section main body 25 and the second pinch portion 35B (the distal-end treatment section 4) rotate in the periaxial directions together with the rotor 26. As described above, the distal-end treatment section 4 and the rotor 26 rotate in the other of the rotating directions with respect to the flexible tube section 5 and the rotor support member 27.

Therefore, the treatment apparatus 1 having the above-described configuration exhibits the following effects. That is, in the treatment apparatus 1 according to this embodiment, the rotor 26 receives the urging force in one of the rotating directions by the action of the torsion spring 71. The rotor 26 and the distal-end treatment section 4 rotate in one of the rotating directions by the urging force from the torsion spring 71. On the other hand, when the rotational operation wire 21A is pulled by an operation using the rotational operation handle 12, the force is applied to the rotor 26 in the oblique direction. The force in the oblique direction is divided into the longitudinal force and the circumferential force acted to the direction opposite to the urging force of the torsion spring 71. The rotor 26 and the distal-end treatment section 4 rotate in the other of the rotating directions by the force acted to the direction opposite to the urging force from the torsion spring 71. As described above, since the distal-end treatment section 4 and the rotor 26 rotate in the periaxial directions with respect to the flexible tube section 5 and the rotor support member 27, the rotational operation is appropriately transmitted to the distal-end treatment section 4. Further, since a motor, a bevel gear, and others are not provided in the distal-end treatment section 4, a diameter of the distal-end treatment section 4 can be reduced. Therefore, it is possible to provide the treatment apparatus 1 that can realize appropriate transmission of the rotational operation to the distal-end treatment section 4 and a reduction of the diameter of the distal-end treatment section 4.

Furthermore, in the treatment apparatus 1, since the distal-end treatment section 4 is rotated in one of the rotating directions by the torsion spring 71, providing one rotational operation wire 21A can suffice. Therefore, a space in the flexible tube section 5 is larger. As a result, for example, when a bending section is provided between the distal-end treatment section 4 and the flexible tube section 5, a bending operation wire and a coil pipe used in the bending operation wire can be readily arranged.

Third Embodiment

A third embodiment according to the present invention will now be described with reference to FIG. 17 and FIG. 18. Like reference numerals denote the same parts and parts having the same functions as those in the first embodiment, thereby omitting a description thereof.

Figure 17:
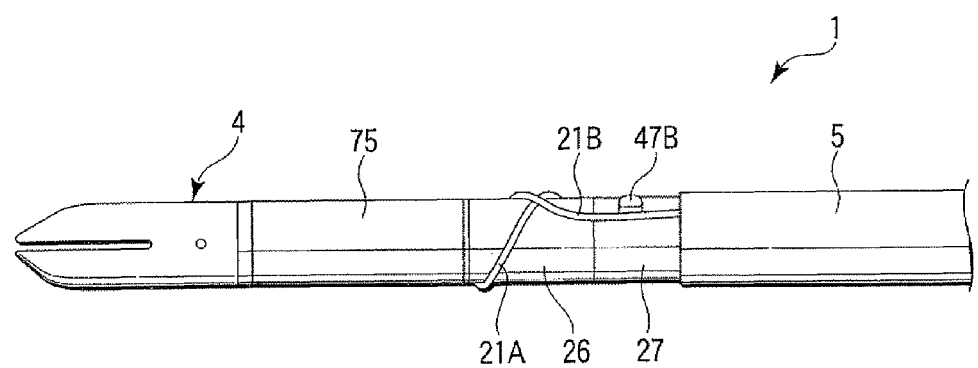
FIG. 17 is a side view schematically showing a configuration of a distal-end direction side part of a treatment apparatus according to a third embodiment of the present invention.

FIG. 17 is a view showing a configuration of a distal-end direction side part of a treatment apparatus 1 according to this embodiment. As shown in FIG. 17, like the first embodiment, the treatment apparatus 1 includes a distal-end treatment section 4, a rotor 26, a rotor support member 27, and a flexible tube section 5. A first rotational operation wire 21A is extended on an outer peripheral surface of the rotor 26 along a first oblique direction. Likewise, a second rotational operation wire 21B is extended on the outer peripheral surface of the rotor 26 along a second oblique direction.

Like the first embodiment, a first convex portion 47A and second convex portion 47B are provided to the rotor support member 27. When the first rotational operation wire 21A abuts on the first convex portion 47A, an extending direction of the first rotational operation wire 21A changes from the first oblique direction. Further, the first rotational operation wire 21A is extended to a rotational operation section (a rotational operation handle 12) through the flexible tube section 5. Furthermore, when the second rotational operation wire 21B abuts on the second convex portion 47B, an extending direction of the second rotational operation wire 21B is changed from the second oblique direction. Moreover, the second rotational operation wire 21B is extended to the rotational operation section (the rotational operation handle 12) through the flexible tube section 5.

As shown in FIG. 17, a tubular portion 75 having flexibility is provided between the distal-end treatment section 4 and the rotor 26. The tubular portion 75 can rotate together with the distal-end treatment section 4 and the rotor 26 in the periaxial directions with respect to the flexible tube section 5 and the rotor support member 27. The distal-end treatment section 4, the rotor 26, and the rotor support member 27 are made of a hard material. Therefore, when the tubular portion 75 is not provided, a dimension of the hard part in the longitudinal directions from a distal end of the treatment apparatus 1 is increased. Therefore, when the tubular portion 75 is provided, the portion having flexibility is provided between the distal-end treatment section 4 and the rotor 26. Therefore, the dimension of the hard portion in the longitudinal directions from the distal end of the treatment apparatus 1 is reduced.

Figure 18:
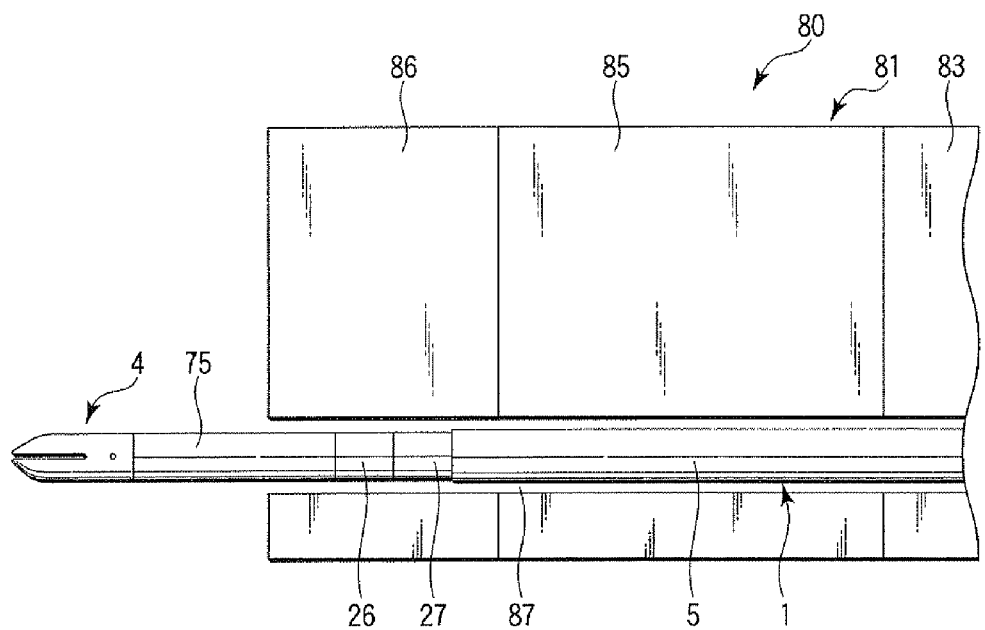
FIG. 18 is a schematic view showing a use state in which the treatment apparatus according to the third embodiment is used together with an endoscope.

FIG. 18 is a view showing a use state in which the treatment apparatus 1 is used together with an endoscope 80. As shown in FIG. 18, the endoscope 80 includes an endoscope insertion section 81 configured to be inserted into a body cavity and an endoscope operation section (not shown) provided to a proximal-end direction side of the endoscope insertion section 81. The endoscope insertion section 81 includes an endoscope flexible tube section 83 having flexibility, an endoscope bending section 85 which is provided to the distal-end direction side of the endoscope flexible tube section 83 and which is configured to perform a bending action, and a distal-end hard section 86 provided to the distal-end direction side of the endoscope bending section 85. An imaging element (not shown) configured to perform an observation of a subject is provided at the distal-end hard section 86. A treatment apparatus insertion channel 87 is extended in the endoscope insertion section 81 along the longitudinal directions. The treatment apparatus 1 is used in a state in which it is inserted in the treatment apparatus insertion channel 87 of the endoscope 80. When using the treatment apparatus 1, the distal-end treatment section 4 of the treatment apparatus 1 is placed at a position in which the distal-end treatment section 4 can be observed (visually confirmed) by the imaging element of the endoscope 80.

As described above, in the treatment apparatus 1, since the tubular portion 75 having the flexibility is provided between the distal-end treatment section 4 and the rotor 26, the longitudinal dimension of the hard portion from the distal end of the treatment apparatus 1 is reduced. Therefore, insertion properties of the treatment apparatus 1 with respect to the treatment apparatus insertion channel 87 of the endoscope 80 can be improved.

Further, in a state that the distal-end treatment section 4 can be observed by the imaging element of the endoscope 80, a proximal end of the rotor support member 27 of the treatment apparatus 1 is placed to the distal-end direction side of a distal end of the endoscope bending section 85. As a result, the flexible tube section 5 having the flexibility in the treatment apparatus 1 is placed in the endoscope bending section 85. Therefore, deterioration of bending properties of the endoscope bending section 85 can be avoided.

It is to be noted that the treatment apparatus 1 may not include the rotor support member 27. In this case, in the state that the distal-end treatment section 4 can be observed by the imaging element of the endoscope 80, a proximal end of the rotor 26 of the treatment apparatus 1 is placed to the distal-end direction side of the distal end of the endoscope bending section 85. That is, in the state that the distal-end treatment section 4 can be observed by the imaging element of the endoscope 80, a distal end of the flexible tube section 5 in the treatment apparatus 1 is placed to the distal-end direction side of the distal end of the endoscope bending section 85.

Fourth Embodiment

A fourth embodiment according to the present invention will now be described with reference to FIG. 19. It is to be noted that like reference numerals denote the same parts or parts having the same functions as those in the first embodiment, thereby omitting a description thereof.

Figure 19:
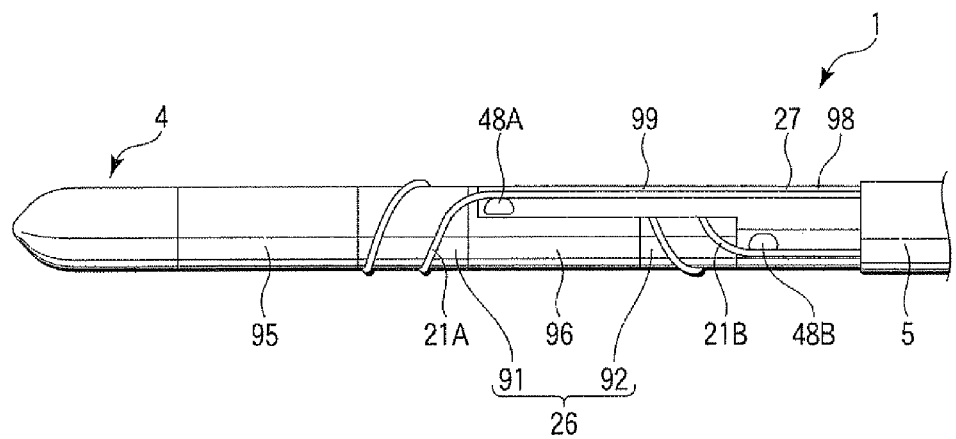
FIG. 19 is a plan view schematically showing a configuration of a distal-end direction side part of a treatment apparatus according to a fourth embodiment of the present invention.

FIG. 19 is a view showing a configuration of a distal-end direction side part of a treatment apparatus 1 according to this embodiment. As shown in FIG. 19, the treatment apparatus 1 includes a distal-end treatment section 4, a flexible tube section 5, a rotor 26, and a rotor support member 27. The rotor 26 includes a first rotor 91 and a second rotor 92 provided to the proximal-end direction side of the first rotor 91. A first tubular portion 95 having flexibility is provided between the first rotor 91 and the distal-end treatment section 4. When the first tubular portion 95 is provided, a dimension of a hard part in the longitudinal directions from a distal end of the treatment apparatus 1 is reduced. Therefore, insertion properties of the treatment apparatus 1 with respect to a treatment apparatus insertion channel of an endoscope can be improved. Further, a second tubular portion 96 having flexibility is provided between the first rotor 91 and the second rotor 92. As a result, the first rotor 91 and the second rotor 92 are arranged in a state that these rotors are apart from each other in the longitudinal directions. The distal-end treatment section 4, the first rotor 91, the second rotor 92, the first tubular portion 95, and the second tubular portion 96 can rotate in the periaxial directions with respect to the flexible tube section 5 and the rotor support member 27.

The rotor support member 27 provided between the second rotor 92 and the flexible tube section 5 includes a member main body 98 and a protruding portion 99 protruding from the member main body 98 to the distal-end direction. A distal end of the protruding portion 99 is extended to a position substantially equal to that of the second tubular portion 96 in the longitudinal directions. A first convex portion 47A is provided to the protruding portion 99 of the rotor support member 27. Further, a second convex portion 47B is provided to the member main body 98 of the rotor support member 27.

A first rotational operation wire 21A is extended on an outer peripheral surface of the first rotor 91 along a first oblique direction. The extending direction of the first rotational operation wire 21A is changed from the first oblique direction when the first rotational operation wire 21A abuts on the first convex portion 47A. Furthermore, the first rotational operation wire 21A is extended to a rotational operation section (a rotational operation handle 12) through the protruding portion 99 of the rotor support member 27 and the flexible tube section 5. Moreover, a second rotational operation wire 21B is extended on an outer peripheral surface of the second rotor 92 along a second oblique direction. The extending direction of the second rotational operation wire 21B is changed from the second oblique direction when the second rotational operation wire 21B abuts on the second convex portion 47B. Additionally, the second rotational operation wire 21B is extended to the rotational operation section (the rotational operation handle 12) through the flexible tube section 5.

At the time of a treatment using the treatment apparatus 1, rotating the distal-end treatment section 4 equal to or above 360° may be required. In such a case, each of the first rotational operation wire 21A and the second rotational operation wire 21B is wound around the outer peripheral surface of the rotor 26 in two or more turns and extended in this state. Therefore, when the first rotational operation wire 21A and the second rotational operation wire 21B are extended on the outer peripheral surface of one rotor 26 like the first embodiment, the first rotational operation wire 21A and the second rotational operation wire 21B cross each other at two positions. As a result, friction between the first rotational operation wire 21A and the second rotational operation wire 21B is increased.

Therefore, in this embodiment, the first rotor 91 and the second rotor 92 are provided. Further, the first rotational operation wire 21A is extended on the outer peripheral surface of the first rotor 91, and the second rotational operation wire 21B is extended on the outer peripheral surface of the second rotor 92. Therefore, when the first rotational operation wire 21A is wound around the outer peripheral surface of the first rotor 91 in two or more turns and the second rotational operation wire 21B is wound around the outer peripheral surface of the second rotor 92 in two or more turns, the first rotational operation wire 21A and the second rotational operation wire 21B do not cross each other. Therefore, friction is not produced between the first rotational operation wire 21A and the second rotational operation wire 21B, and the distal-end treatment section 4 can be rotated equal to or above 360°.

Fifth Embodiment

A fifth embodiment according to the present invention will now be described with reference to FIG. 20. It is to be noted that like reference numerals denote the same parts and parts having the same functions as those in the fourth embodiment, thereby omitting a description thereof.

Figure 20:
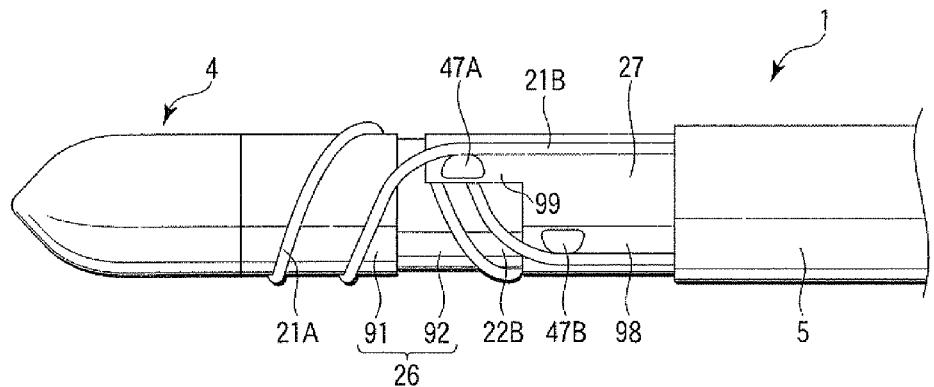
FIG. 20 is a plan view schematically showing a configuration of a distal-end direction side part of a treatment apparatus according to a fifth embodiment of the present invention.

FIG. 20 is a view showing a configuration of a distal-end direction side part of a treatment apparatus 1 according to this embodiment. As shown in FIG. 20, the treatment apparatus 1 includes a distal-end treatment section 4, a flexible tube section 5, a first rotor 91, a second rotor 92, and a rotor support member 27. The second rotor 92 is provided in a state that the first rotor 91 is continuous to the distal-end direction side. The distal-end treatment section 4, the first rotor 91, and the second rotor 92 can rotate in the periaxial directions with respect to the flexible tube section 5 and the rotor support member 27.

The rotor support member 27 includes a member main body 98 and a protruding portion 99. A distal end of the protruding portion 99 is extended to a position substantially equal to that of the second rotor 92 in the longitudinal directions. A first convex portion 47A is provided to the protruding portion 99 of the rotor support member 27, and a second convex portion 47B is provided to the member main body 98 of the rotor support member 27.

A first rotational operation wire 21A is extended on an outer peripheral surface of the first rotor 91 along a first oblique direction. When the first rotational operation wire 21A abuts on the first convex portion 47A, the extending direction of the first rotational operation wire 21A is changed from the first oblique direction. Further, the first rotation operation wire 21A is extended to a rotational operation section (a rotational operation handle 12) through the flexible tube section 5. Moreover, a second rotational operation wire 21B is extended on an outer peripheral surface of the second rotor 92 along a second oblique direction. When the second rotational operation wire 21B abuts on the second convex portion 47B, the extending direction of the second rotational operation wire 21B is changed from the second oblique direction. Additionally, the second rotational operation wire 21B is extended to the rotational operation section (the rotational operation handle 12) through the flexible tube section 5.

In the treatment apparatus 1 according to this embodiment, the first rotor 91 and the second rotor 92 are separately provided. Further, the first rotational operation wire 21A is extended on the outer peripheral surface of the first rotor 91, and the second rotational operation wire 21B is extended on the outer peripheral surface of the second rotor 92. Therefore, even when the first rotational operation wire 21A is wound around the outer peripheral surface of the first rotor 91 in two or more turns and the second rotational operation wire 21B is wound around the outer peripheral surface of the second rotor 92 in two or more turns, the first rotation operation wire 21A does not cross the second rotational operation wire 21B. Therefore, friction is not produced between the first rotational operation wire 21A and the second rotational operation wire 21B, and the distal-end treatment section 4 can be rotated equal to or above 360°.

Here, in the treatment apparatus 1 according to the fourth embodiment, since the second tubular portion 96 is provided, the dimension in the longitudinal directions from the second rotor 92 to the distal-end treatment section 4 is increased. Therefore, a rotational action of the second rotor 92 may possibly not be appropriately transmitted to the distal-end treatment section 4. In this case, the rotation tracking properties of the distal-end treatment section 4 with respect to the second rotor 92 are reduced, and operability of the rotational operation is deteriorated.

Therefore, in this embodiment, the first rotor 91 is continuous to the distal-end direction side of the second rotor 92, and the second tubular portion 96 is not provided. Accordingly, the dimension in the longitudinal directions from the second rotor 92 to the distal-end treatment section 4 can be reduced. Therefore, not only the rotational action of the first rotor 91 but also the rotational action of the second rotor 92 placed to the proximal-end direction side can be appropriately transmitted to the distal-end treatment section 4. Therefore, the rotation tracking properties of the distal-end treatment section 4 with respect to the second rotor 92 can be improved. As a result, when rotating the distal-end treatment section 4 equal to or above 360°, the operability of the rotational operation can be assured.

It is to be noted that, to reduce the dimension of the hard part of the treatment apparatus 1 in the longitudinal directions from the distal end, a tubular portion having flexibility may be provided between the distal-end treatment section 4 and the first rotor 91. In this case, the tubular portion rotates together with the distal-end treatment section 4, the first rotor 91, and the second rotor 92 in the periaxial directions with respect to the flexible tube section 5.

First Reference Example

A first reference example will now be described with reference to FIG. 21. Like reference numerals denote the same parts and parts having the same functions as those in the first embodiment, thereby omitting a description thereof.

Figure 21:
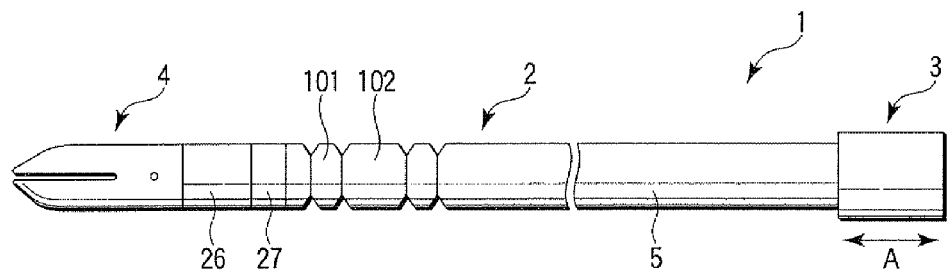
FIG. 21 is a schematic view showing a treatment apparatus according to a first reference example.

FIG. 21 is a view showing a treatment apparatus 1 according to this reference example. As shown in FIG. 21, the treatment apparatus 1 according to this reference example includes a first bending section 101 and a second bending section 102 provided between a rotor support member 27 and a flexible tube section 5. The first bending section 101 is provided to the distal-end direction side of the second bending section 102. The first bending section 101 is a bending section with two freedom degrees configured to perform a bending action in four directions. Likewise, the second bending section 102 is a bending section with two freedom degrees configured to perform a bending action in four directions. The first bending section 101 and the second bending section 102 carry out the bending action by pulling or loosening a bending operation wire (not shown).

A distal-end treatment section 4 and a rotor 26 rotate in the periaxial directions with respect to a flexible tube section 5 by pulling or loosening a first rotational operation wire 21A and a second rotational operation wire 21B like the first embodiment. Moreover, when an operation section 3 is moved in the longitudinal directions (an arrowhead A in FIG. 21), the distal-end treatment section 4 moves forward and backward in the longitudinal directions.

As described above, in the treatment apparatus 1, the bending actions of the first bending section 101 and the second bending section 102 and the rotational action of the distal-end treatment section 4 are carried out by pulling or loosening the operation wires (the bending operation wire and the rotational operation wires 21A and 21B). For example, when rotating the operation section 3 to rotate the distal-end treatment section 4, the rotational operation in the operation section 3 may possibly not be appropriately transmitted to the distal-end treatment section 4 due to, e.g., a change in shape of an insertion section 2 at the time of insertion into a body cavity. Therefore, in this reference example, the distal-end treatment section 4 is rotated by pulling or loosening the first rotational operation wire 21A and the second rotational operation wire 21B. Therefore, the rotational operation in the operation section is appropriately transmitted to the distal-end treatment section 4 irrespective of a shape of the insertion section 2. This is also true for the bending operations of the first bending section 101 and the second bending section 102.

Second Reference Example

A second reference example will now be described with reference to FIG. 22. It is to be noted that like reference numerals denote the same parts and parts having the same functions as those in the first reference example, thereby omitting a description thereof.

Figure 22:
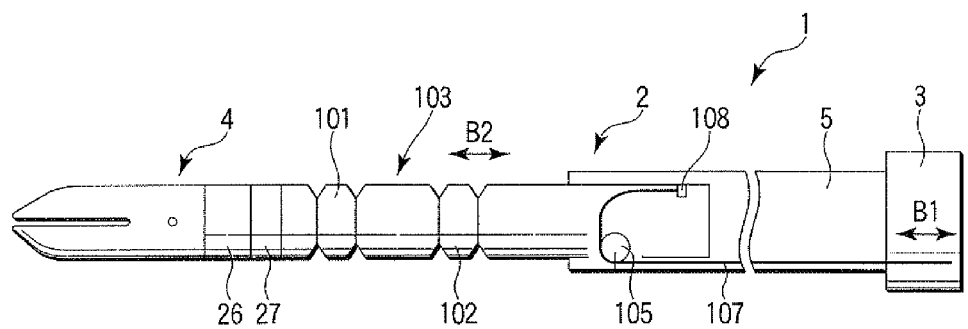
FIG. 22 is a schematic view showing a treatment apparatus according to a second reference example.

FIG. 22 is a view showing a treatment apparatus 1 according to this reference example. As shown in FIG. 21, the treatment apparatus 1 according to this reference example includes a flexible tube section 5 and an advancing/retreating unit 10 configured to move forward and backward in the longitudinal directions with respect to a flexible tube section 5. The advancing/retreating unit 103 is provided to the distal-end direction side of the flexible tube section 5. The advancing/retreating unit 103 includes a distal-end treatment section 4, a rotor 26, a rotor support member 27, a first bending section 101, and a second bending section 102.

Each of the first bending section 101 and the second bending section 102 is configured to perform a bending action by pulling or loosening a bending operation wire (not shown). The distal-end treatment section 4 and the rotor 26 rotate in the periaxial directions with respect to the flexible tube section 5 by pulling or loosening a first rotational operation wire 21A and a second rotational operation wire 21B like the first embodiment.

An advancing/retreating operation wire 107 configured to advance or retreat the advancing/retreating unit 103 with respect to the flexible tube section 5 is extended in the flexible tube section 5 along the longitudinal directions. One end of the advancing/retreating operation wire 107 is connected to an operation section 3. The advancing/retreating operation wire 107 extended from the operation section 3 to the distal-end direction is folded toward the proximal-end direction by a pulley 105 fixed in the flexible tube section 5. Further, the other end of the advancing/retreating operation wire 107 is fixed to a fixing portion 108 of the advancing/retreating unit 103.

Adopting such a configuration allows the advancing/retreating unit 103 to advance or retreat with respect to the flexible tube section 5 (an arrowhead B2 in FIG. 22) by pulling or loosening the advancing/retreating operation wire 107 (an arrowhead B1 in FIG. 22). As described above, in this reference example, the distal-end treatment section 4 is advanced or retreated by pulling or loosening the advancing/retreating operation wire 107. Therefore, the advancing/retreating operation in the operation section can be appropriately transmitted to the distal-end treatment section 4 irrespective of a shape of an insertion section 2.

Moreover, in this reference example, when each of the operation wires (the bending operation wire, the rotational operation wires 21A and 21B, the advancing/retreating operation wire 107) is pulled or loosened, the bending actions of the first bending section 101 and the second bending section 102, the rotational action of the distal-end treatment section 4, and the advancing/retreating action of the distal-end treatment section 4 are carried out. That is, all four actions are carried out by pulling or loosening the operation wires. Therefore, changes in driving characteristics of the respective operations due to a variation in shape of the insertion section 2 are substantially equal in the respective actions. Therefore, the bending actions of the first bending section 101 and the second bending section 102, the rotational action of the distal-end treatment section 4, and the advancing/retreating action of the distal-end treatment section 4 can be easily performed.

Notes (Additional Note 1)

A treatment apparatus comprising:

a flexible tube section which has a longitudinal axis and is extended in longitudinal directions;

a distal-end treatment section which is provided to a distal-end direction side of the flexible tube section and which is rotatable in periaxial directions with respect to the flexible tube section;

a rotor which is provided between the distal-end treatment section and the flexible tube section and which is rotatable together with the distal-end treatment section in the periaxial directions with respect to the flexible tube section;

a rotational operation section which is provided to a proximal-end direction side of the flexible tube section and which is configured to perform a rotational operation of the distal-end treatment section;

a rotational operation wire which is configured to be pulled or loosened by the rotational operation section to rotate the distal-end treatment section;

a wire fixing portion which is provided to the rotor or to a part to the distal-end direction side of the rotor and to which a distal end of the rotational operation wire is fixed; and a direction change portion which is configured to change an extending direction of the rotational operation wire, extended on an outer peripheral surface of the rotor from the wire fixing portion along an oblique direction inclined from the longitudinal directions toward circumferential directions, from the oblique direction, and configured to lead out the rotational operation wire to the rotational operation section.

(Additional Note 2)

The treatment apparatus according to Additional note 1, further comprising an urging member configured to give the distal-end treatment section an urging force in one of rotating directions, wherein the rotational operation wire is extended on the outer peripheral surface of the rotor from the wire fixing portion along the oblique direction inclined from the longitudinal directions toward the circumferential directions to a direction opposite to a direction where the urging member gives the urging force.

(Additional Note 3)

The treatment apparatus according to Additional note 1, further comprising a tubular portion which is provided between the distal-end treatment section and the rotor and which has flexibility.

(Additional Note 4)

The treatment apparatus according to Additional note 1, wherein the rotor includes a first rotor, and a second rotor provided to the proximal-end direction side of the first rotor, the rotational operation wire includes a first rotational operation wire which is extended on an outer peripheral surface of the first rotor along a first oblique direction, and a second rotational operation wire which is extended on an outer peripheral surface of the second rotor along the second oblique direction inclined from the longitudinal directions toward the circumferential directions to a direction opposite to the first oblique direction, and the direction change portion includes a first direction change portion which is configured to change the extending direction of the first rotational operation wire from the first oblique direction, and a second direction change portion which is configured to change the extending direction of the second rotational operation wire from the second oblique direction.

(Additional Note 5)

The treatment apparatus according to Additional note 4, wherein the second rotor is provided in a state that the first rotor is continuous to the distal-end direction side.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment apparatus comprising:
   a flexible tube section which has a longitudinal axis, and the flexible tube section being extended in longitudinal directions;
   a distal-end treatment section which is provided to a distal-end direction side of the flexible tube section, and the distal-end treatment section being rotatable in directions around the longitudinal axis with respect to the flexible tube section;
   a rotor which is provided between the distal-end treatment section and the flexible tube section, and the rotor being rotatable together with the distal-end treatment section in the directions around the longitudinal axis with respect to the flexible tube section;
   a rotational operation section which is provided to a proximal-end direction side of the flexible tube section, and the rotational operation section being configured to perform a rotational operation of the distal-end treatment section;
   a rotational operation wire which is extended on an outer peripheral surface of the rotor along a predetermined extending direction, and the rotational operation wire being configured to be pulled by the rotational operation section to apply force to the rotor in one of the directions around the longitudinal axis, the distal-end treatment section and the rotor being configured to rotate by the force applied in one of the directions around the longitudinal axis;
   a wire fixing portion which is provided to the rotor or to a part to the distal-end direction side of the rotor, and to which a distal end of the rotational operation wire is fixed; and
   a direction change portion which is configured to change an extending direction of the rotational operation wire, extended toward the outer peripheral surface of the rotor from the wire fixing portion, from the predetermined extending direction at apart to the proximal-end direction side of the rotor, and the direction change portion being configured to lead out the rotational operation wire, whose extending direction is changed from the predetermined extending direction, toward the rotational operation section.

2. The treatment apparatus according to claim 1, further comprising:
   a wire inserting portion through which the rotational operation wire, whose extending direction has been changed from an oblique direction inclined from the longitudinal directions to circumferential directions by the direction change portion, is inserted into the flexible tube section.

3. The treatment apparatus according to claim 1,
   wherein the direction change portion includes a convex portion which is provided on an outer peripheral surface of a distal-end direction side part of the flexible tube section or an outer peripheral surface of a different member fixed the flexible tube section and provided between the flexible tube section and the rotor and which protrudes toward an outer peripheral direction, the convex portion being configured to abut on the rotational operation wire extended on the outer peripheral surface of the rotor to change the extending direction of the rotational operation wire.

4. The treatment apparatus according to claim 3,
   wherein the convex portion includes a circular surface on which the rotational operation wire abuts.

5. The treatment apparatus according to claim 3,
   wherein the rotational operation wire includes a first rotational operation wire which is extended from the wire fixing portion on the outer peripheral surface of the rotor along a first oblique direction inclined from the longitudinal directions toward the circumferential directions, and a second rotational operation wire which is extended on the outer peripheral surface of the rotor from the wire fixing portion along a second oblique direction inclined from the longitudinal directions toward the circumferential directions to a direction opposite to the first oblique direction, and
   the convex portion includes a first convex portion on which the first rotational operation wire abuts, and a second convex portion on which the second rotational operation wire abuts.

6. The treatment apparatus according to claim 5,
wherein the rotor includes a wire crossing portion at which the first rotational operation wire is configured to cross the second rotational operation wire on the outer peripheral surface.

7. The treatment apparatus according to claim 6,
wherein the first convex portion includes a first root which is placed to be radially apart from the longitudinal axis of the flexible tube section by a first distance, and
the second convex portion includes a second root which is placed to be radially apart from the longitudinal axis of the flexible tube section by a second distance smaller than the first distance, a difference of the second distance from the first distance being not smaller than a diameter of each of the first rotational operation wire and the second rotational operation wire.

8. The treatment apparatus according to claim 3,
wherein the outer peripheral surface of the flexible tube section includes a convex portion arrangement surface which has a smaller radial distance from the longitudinal axis of the flexible tube section than that of any other portions of the outer peripheral surface and on which the convex portion is placed.

9. The treatment apparatus according to claim 3,
wherein the outer peripheral surface of the different member provided to be fixed the flexible tube section has a convex portion arrangement surface which has a smaller radial distance from the longitudinal axis of the flexible tube section than that of any other portions of the outer peripheral surface and on which the convex portion is placed.

\* \* \* \* \*